US012318509B2

United States Patent
Rinaldi et al.

(10) Patent No.: US 12,318,509 B2
(45) Date of Patent: Jun. 3, 2025

(54) MAGNETICALLY TEMPLATED TISSUE ENGINEERING SCAFFOLDS AND METHODS OF MAKING AND USING THE MAGNETICALLY TEMPLATED TISSUE ENGINEERING SCAFFOLDS

(71) Applicant: University of Florida Research Foundation, Inc., Gainesville, FL (US)

(72) Inventors: Carlos Rinaldi, Gainesville, FL (US); Christine E. Schmidt, Gainesville, FL (US); Christopher Lacko, Gainesville, FL (US); Zin Khaing, Lake Forest Park, WA (US); Andrew Garcia, Orlando, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 87 days.

(21) Appl. No.: 17/161,952

(22) Filed: Jan. 29, 2021

(65) Prior Publication Data
US 2021/0178024 A1 Jun. 17, 2021

Related U.S. Application Data

(62) Division of application No. 15/573,270, filed as application No. PCT/US2016/031794 on May 11, 2016, now Pat. No. 10,918,767.

(Continued)

(51) Int. Cl.
*A61L 27/52* (2006.01)
*A61B 17/11* (2006.01)
(Continued)

(52) U.S. Cl.
CPC .......... *A61L 27/56* (2013.01); *A61B 17/1128* (2013.01); *A61L 27/20* (2013.01);
(Continued)

(58) Field of Classification Search
CPC .......... A61L 27/52; A61L 27/56; A61L 27/58; A61L 2430/32; A61B 17/1128
See application file for complete search history.

(56) References Cited

U.S. PATENT DOCUMENTS

| 8,399,229 B2 | 3/2013 | Sooryakumar et al. |
| 8,652,215 B2 | 2/2014 | Bellamkonda et al. |

(Continued)

FOREIGN PATENT DOCUMENTS

| WO | 1989010728 A1 | 11/1989 |
| WO | WO2010098633 A2 | 9/2010 |
| WO | WO2011156895 A2 | 12/2011 |

OTHER PUBLICATIONS

J. S. Belkas, M. S. Shoichet, and R. Midha, "Axonal guidance channels in peripheral nerve regeneration," Operative Techniques in Orthopaedics, vol. 14, pp. 190-198, Jul. 2004.

(Continued)

*Primary Examiner* — Todd J Scherbel
(74) *Attorney, Agent, or Firm* — Alston & Bird LLP

(57) ABSTRACT

The present disclosure provides magnetically templated tissue scaffolds, methods of making the magnetically templated tissue scaffolds, and various methods of employing the scaffolds for tissue growth and repair in vitro and in vivo, including peripheral nerve repair.

11 Claims, 6 Drawing Sheets

MAMs include iron oxide nanoparticles (IONPs) embedded in calcium alginate | MAMs dispersed in pre-hydrogel mixture in the absence of magnetic field | Formation of aligned MAM columnar structures and UV crosslinking under applied magnetic field | MAM dissolution and diffusion of IONPs out of the hydrogels | Aligned microchannels remain after complete MAM dissolution and IONP diffusion

Related U.S. Application Data

(60) Provisional application No. 62/160,202, filed on May 12, 2015.

(51) Int. Cl.
```
A61L 27/20    (2006.01)
A61L 27/24    (2006.01)
A61L 27/26    (2006.01)
A61L 27/56    (2006.01)
A61L 27/58    (2006.01)
```
(52) U.S. Cl.
CPC .............. *A61L 27/24* (2013.01); *A61L 27/26* (2013.01); *A61L 27/52* (2013.01); *A61L 27/58* (2013.01); *A61L 2400/08* (2013.01); *A61L 2430/32* (2013.01)

(56) References Cited

U.S. PATENT DOCUMENTS

| | | | |
|---|---|---|---|
| 8,889,761 | B2 | 11/2014 | Studart et al. |
| 9,051,549 | B2 | 6/2015 | Grogan et al. |
| 2008/0213389 | A1 | 9/2008 | Lelkes et al. |
| 2010/0068740 | A1 | 3/2010 | Kaplan et al. |
| 2011/0076665 | A1 | 3/2011 | Gatenholm et al. |
| 2011/0129515 | A1* | 6/2011 | Archibald ............... A61L 27/26 514/17.7 |
| 2012/0146632 | A1 | 6/2012 | Gleich |
| 2012/0149111 | A1 | 6/2012 | Wegst et al. |
| 2013/0053471 | A1 | 2/2013 | Studart et al. |
| 2014/0193468 | A1* | 7/2014 | Tarrant ................. A61L 27/3817 514/17.1 |
| 2014/0234388 | A1* | 8/2014 | Christ ..................... A61K 33/26 264/41 |
| 2015/0104872 | A1* | 4/2015 | Smith .................. C12N 5/0655 435/395 |

OTHER PUBLICATIONS

S. Ichihara, Y. Inada, and T. Nakamura, "Artificial nerve tubes and their application for repair of peripheral nerve injury: an update of current concepts," Injury, vol. 39, pp. 29-39, Oct. 2008.

K. Brattain, "Analysis of the Peripheral Nerve Injury Market in the United States," Magellan Medical Technology Consultants, Inc., Minneapolis, MN, 2013.

S. K. Lee and S. W. Wolfe, "Peripheral nerve injury and repair," J Am Acad Orthop Surg, vol. 8, pp. 243-252, Jul.-Aug. 2000.

T. W. Hudson, S. Y. Liu, and C. E. Schmidt, "Engineering an improved acellular nerve graft via optimized chemical processing," Tissue engineering, vol. 10, pp. 1346-1358, 2004.

T. W. Hudson, S. Zawko, C. Deister, S. Lundy, C. Y. Hu, K. Lee, and C. E. Schmidt, "Optimized acellular nerve graft is immunologically tolerated and supports regeneration," Tissue engineering, vol. 10, pp. 1641-1651, 2004.

D. N. Brooks, R. V. Weber, J. D. Chao, B. D. Rinker, J. Zoldos, M. R. Robichaux, S. B. Ruggeri, K. A. Anderson, E. E. Bonatz, S. M. Wisotsky, M. S. Cho, C. Wilson, E. O. Cooper, J. V. Ingari, B. Safa, B. M. Parrett, and G. M. Buncke, "Processed nerve allografts for peripheral nerve reconstruction: a multicenter study of utilization and outcomes in sensory, mixed, and motor nerve reconstructions," Microsurgery, vol. 32, pp. 1-14, Jan. 2012.

E. C. Spivey, Z. Z. Khaing, J. B. Shear, and C. E. Schmidt, "The fundamental role of subcellular topography in peripheral nerve repair therapies," Biomaterials, vol. 33, pp. 4264-4276, Jul. 1, 2012.

S. Kehoe, X. F. Zhang, and D. Boyd, "FDA approved guidance conduits and wraps for peripheral nerve injury: A review of materials and efficacy," Injury, vol. 43, pp. 553-572, Jun. 1, 2012.

D. Hoffman-Kim, J. A. Mitchel, and R. V. Bellamkonda, "Topography, Cell Response, and Nerve Regeneration," Annual Review of Biomedical Engineering, vol. 12, pp. 203-231, Jul. 2010.

V. Mukhatyar, L. Karumbaiah, J. Yeh, and R. Bellamkonda, "Tissue Engineering Strategies Designed to Realize the Endogenous Regenerative Potential of Peripheral Nerves," Advanced Materials, pp. NA-NA, Nov. 10, 2009.

T. Hadlock, C. Sundback, D. Hunter, M. Cheney, and J. P. Vacanti, "A polymer foam conduit seeded with Schwann cells promotes guided peripheral nerve regeneration," Tissue Eng, vol. 6, pp. 119-127, Apr. 2000.

S. Stokols and M. H. Tuszynski, "Freeze-dried agarose scaffolds with uniaxial channels stimulate and guide linear axonal growth following spinal cord injury," Biomaterials, vol. 27, pp. 443-451, Feb. 2006.

J. B. Scott, M. Afshari, R. Kotek, and J. M. Saul, "The promotion of axon extension in vitro using polymer-templated fibrin scaffolds," Biomaterials, vol. 32, pp. 4830-4839, Jul. 1, 2011.

K. T. Morin and R. T. Tranquillo, "Guided sprouting from endothelial spheroids in fibrin gels aligned by magnetic fields and cell-induced gel compaction," Biomaterials, vol. 32, pp. 6111-6118, Sep. 1, 2011.

N. Dubey, P. C. Letourneau, and R. T. Tranquillo, "Guided neurite elongation and Schwann cell invasion into magnetically aligned collagen in simulated peripheral nerve regeneration," Experimental neurology, vol. 158, pp. 338-350, 1999.

D. Ceballos, X. Navarro, N. Dubey, G. Wendelschafer-Crabb, W. R. Kennedy, and R. T. Tranquillo, "Magnetically aligned collagen gel filling a collagen nerve guide improves peripheral nerve regeneration," Experimental neurology, vol. 158, pp. 290-300, 1999.

R. T. Tranquillo, T. S. Girton, B. A. Bromberek, T. G. Triebes, and D. L. Mooradian, "Magnetically orientated tissue-equivalent tubes: application to a circumferentially orientated media-equivalent," Biomaterials, vol. 17, pp. 349-357, 1996.

M. R. Sommer, R. M. Erb, and A. R. Studart, "Injectable Materials with Magnetically Controlled Anisotropic Porosity," ACS Applied Materials Interfaces, vol. 4, pp. 5086-5091, Oct. 24, 2012.

Y. Li, G. Huang, X. Zhang, B. Li, Y. Chen, T. Lu, T. J. Lu, and F. Xu, "Magnetic Hydrogels and Their Potential Biomedical Applications," Advanced Functional Materials, vol. 23, pp. 660-672, Sep. 27, 2012.

C. Hu, C. Tercero, S. Ikeda, M. Nakajima, H. Tajima, Y. Shen, T. Fukuda, and F. Arai, "Biodegradable porous sheet-like scaffolds for soft-tissue engineering using a combined particulate leaching of salt particles and magnetic sugar particles," JBIOSC, vol. 116, pp. 126-131, Jul. 1, 2013.

C. Hu, T. Uchida, C. Tercero, S. Ikeda, K. Ooe, T. Fukuda, F. Arai, M. Negoro, and G. Kwon, "Development of biodegradable scaffolds based on magnetically guided assembly of magnetic sugar particles," Journal of Biotechnology, vol. 159, pp. 90-98, Jun. 31, 2012.

B. R. Whatley, X. Li, N. Zhang, and X. Wen, "Magnetic-directed patterning of cell spheroids," Journal of Biomedical Materials Research Part A, vol. 102, pp. 1537-1547, Jul. 2, 2013.

S. Tasoglu, D. Kavaz, U. A. Gurkan, S. Guven, p. Chen, R. Zheng, and U. Demirci, "Paramagnetic Levitational Assembly of Hydrogels," Advanced Materials, vol. 25, pp. 1137-1143, Dec. 10, 2012.

L. H. Reddy, J. L. Arias, J. Nicolas, and p. Couvreur, "Magnetic Nanoparticles: Design and Characterization, Toxicity and Biocompatibility, Pharmaceutical and Biomedical Applications," Chemical Reviews, vol. 112, pp. 5818-5878, Nov. 14, 2012.

N. Lewinski, V. Colvin, and R. Drezek, "Cytotoxicity of Nanoparticles," Small, vol. 4, pp. 26-49, Feb. 18, 2008.

W. R. Gombotz and S. F. Wee, "Protein release from alginate matrices," Advanced Drug Delivery Reviews, vol. 64, pp. 194-205, 2012.

H. H. Tønnesen and J. Karlsen, "Alginate in drug delivery systems," Drug development and industrial pharmacy, vol. 28, pp. 621-630, 2002.

C. Bucke, "Cell Immobilization in Calcium Alginate," Methods in enzymology, vol. 135, pp. 175-189, 1987.

Z. Z. Khaing and C. E. Schmidt, "Advances in natural biomaterials for nerve tissue repair," Neuroscience Letters, vol. 519, pp. 103-114, Jul. 25, 2012.

S. K. Seidlits, Z. Z. Khaing, R. R. Petersen, J. D. Nickels, J. E. Vanscoy, J. B. Shear, and C. E. Schmidt, "The effects of hyaluronic

(56) References Cited

OTHER PUBLICATIONS acid hydrogels with tunable mechanical properties on neural progenitor cell differentiation," Biomaterials, vol. 31, pp. 3930-3940, Jun. 1, 2010.
A. P. Herrera, C. Barrera, and C. Rinaldi, "Synthesis and functionalization of magnetite nanoparticles with aminopropylsilane and carboxymethyldextran," Journal of Materials Chemistry, vol. 18, p. 3650, 2008.
V. L. Calero-DdelC, A. M. Gonzalez, and C. Rinaldi, "A Statistical Analysis to Control the Growth of Cobalt Ferrite Nanoparticles Synthesized by the Thermodecomposition Method," Journal of Manufacturing Science and Engineering, vol. 132, p. 030914, 2010.
C. E. Schmidt and J. B. Leach, "Neural tissue engineering: strategies for repair and regeneration," Annu Rev Biomed Eng, vol. 5, pp. 293-347, 2003.
S. Suri and C. E. Schmidt, "Photopatterned collagen-hyaluronic acid interpenetrating polymer network hydrogels," Acta Biomater, vol. 5, pp. 2385-2397, Sep. 2009.
P. Danhier, G. De Preter, S. Boutry, I. Mahieu, p. Leveque, J. Magat, V. Haufroid, P. Sonveaux, C. Bouzin, O. Feron, R. N. Muller, B. F. Jordan, and B. Gallez, "Electron paramagnetic resonance as a sensitive tool to assess the iron oxide content in cells for MRI cell labeling studies," Contrast media molecular imaging, vol. 7, pp. 302-307, May 26, 2012.
V. Ayala, A. P. Herrera, M. Latorre-Esteves, M. Torres-Lugo, and C. Rinaldi, "Effect of surface charge on the colloidal stability and in vitro uptake of carboxymethyl dextran-coated iron oxide nanoparticles," Journal of Nanoparticle Research, vol. 15, p. 1874, Jul. 30, 2013.
S. K. Seidlits, C. E. Schmidt, and J. B. Shear, "High-Resolution Patterning of Hydrogels in Three Dimensions using Direct-Write Photofabrication for Cell Guidance," Advanced Functional Materials, vol. 19, pp. 3543-3551, Nov. 23, 2009.
P. Dinh, A. Hazel, W. Palispis, S. Suryadevara, and R. Gupta, "Functional assessment after sciatic nerve injury in a rat model," Microsurgery, vol. 29, pp. 644-649, 2009.
Madigan, et al., "Current tissue engineering and novel therapeutic approaches to axonal regeneration following spinal cord injury using polymer scaffolds," Respiratory Physiology & Neurobiology: vol. 169, Issue 2, Nov. 30, 2009, pp. 183-199.
Tabesh, et al. "The role of biodegradable engineered scaffolds seeded with Schwann cells for spinal cord regeneration," Neurochemistry International: vol. 54, Issue 2, Feb. 2009, pp. 73-83.
Hollister, "Porous scaffold design for tissue engineering," Nature Materials 4, 518-524 (2005).
Kim, et al., "Magnetic scaffolds of polycaprolactone with functionalized magnetite nanoparticles: physicochemical, mechanical, and biological properties effective for bone regeneration," RSC Advances: An international journal to further the chemical sciences, Issue 33, 2014, RSC Adv., 2014,4, 17325-17336.
Yang, et al., "The Design of Scaffolds for Use in Tissue Engineering. Part I. Traditional Factors," Tissue Engineering. Dec. 2001, vol. 7 Issue 6: 679-689.
Bock, et al., "A novel route in bone tissue engineering: Magnetic biomimetic scaffolds," Acta Biomaterialia. vol. 6, Issue 3, Mar. 2010, pp. 786-796.
Ito, et al., Tissue Engineering Using Magnetite Nanoparticles and Magnetic Force: Heterotypic Layers of Cocultured Hepatocytes and Endothelial Cells, vol. 10 Issue 5-6: Aug. 25, 2004.
International Search Report for PCT/US2016/031794 mailed Aug. 5, 2016.
Alsberc, et al., "Magnetically-Guided Self-Assembly of Fibrin Matrices with Ordered Nano-Scale Structure for Tissue Engineering", Tissue Engineering, vol. 12, No. 11, 2006, pp. 3247-3256.
Dubey, et al., "Guided Neurite Elongation and Schwann Cell Invasion into Magnetically Aligned Collagen in Simulated Peripheral Nerve Regeneration", Experimental Neurology, 158, 338-35, 1999.
Willerth, et al., "Approaches to Neural tissue Engineering Using Scaffolds for Drug Delivery", NIH, Adv Drug Deliv Ref. May 3, 20070; 59(4-5); 325-338, 27 pages.
Mérida, et al., "Optimization of Synthesis and Peptization Steps to Obtain Iron Oxide Nanoparticles with High Specific Absorption Rates", *Journal of Magentism and Magnetic Materials*, vol. 394, pp. 361-371, Nov. 15, 2015, doi: 10.1016/j.jmmm.2015.06.076.
Flynn, et al., "Fiber Templating of Poly(2-hydroxyethyl methacrylate) for Neural Tissue Engineering", *Biomaterials*, vol. 24, pp. 4265-4272, (2003), doi: 10.1016/S0142-9612(03)00334-X.
Pien, et al., "Tissue Engineering of Skeletal Muscle, Tendons and Nerves: A Review of Manufacturing Strategies to Meet Structural and Functional Requirements", *Applied Materials Today*, vol. 31, Feb. 10, 2023, (38 pages), https://doi.org/10.1016/j.apmt.2023.101737.
Lacko, et al., "Magnetic Particle Templating of Hydrogels: Engineering Naturally Derived Hydrogel Scaffolds with 3D Aligned Microarchitecture for Nerve Repair", *J. Neural Eng.*, vol. 17(1):016057, (26 pages), Feb. 12, 2021, doi:10.1088/1741-2552/ab4a22.
Sridharan, et al., "Decellularized Grafts with Axially Aligned Channels for Peripheral Nerve Regeneration", *J. Mech. Behav. Biomed. Mater.*, vol. 41, pp. 124-135, (2015).

\* cited by examiner

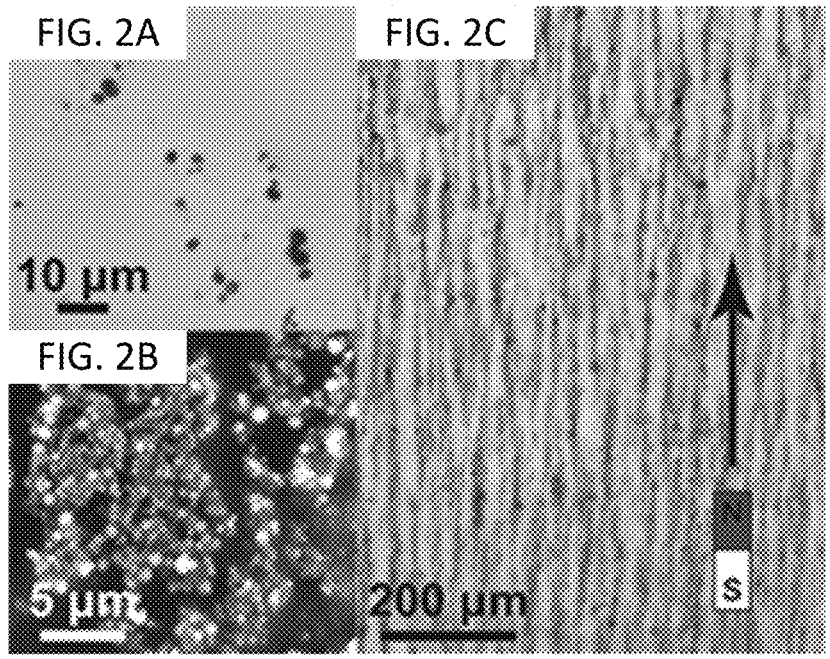
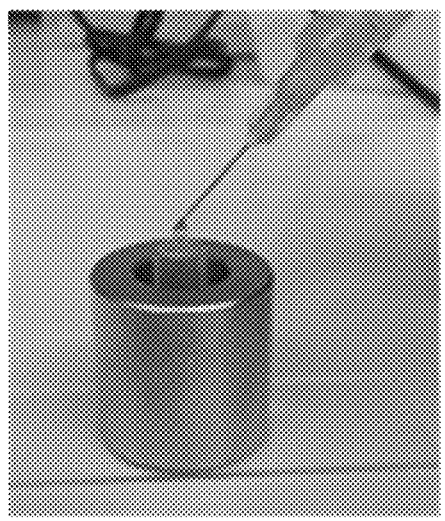
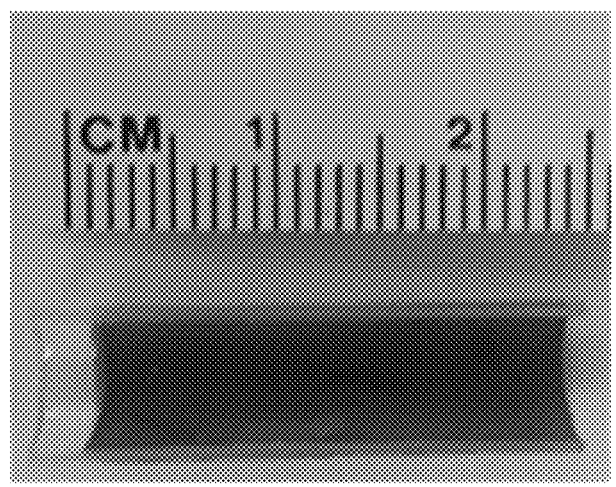
FIG. 3A					FIG. 3B

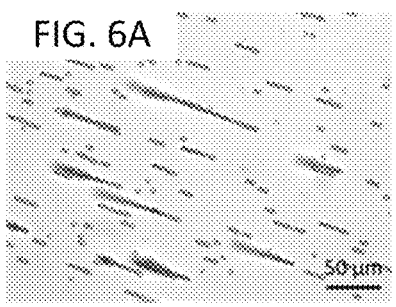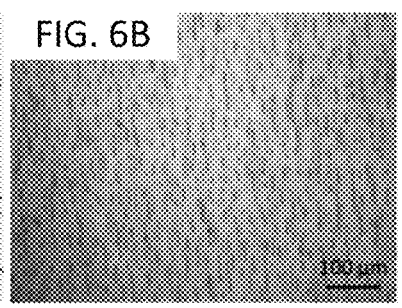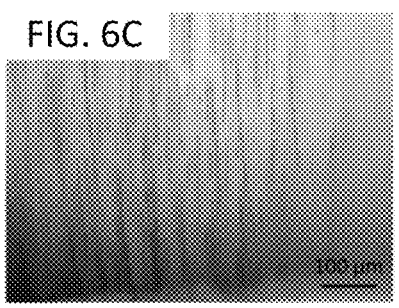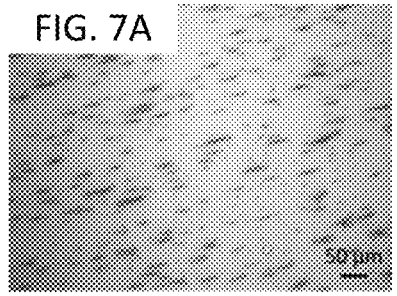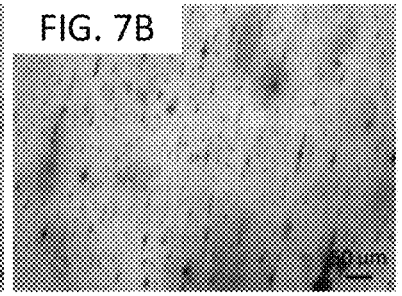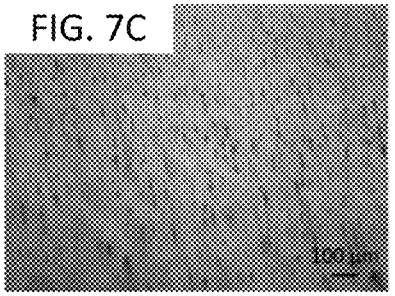

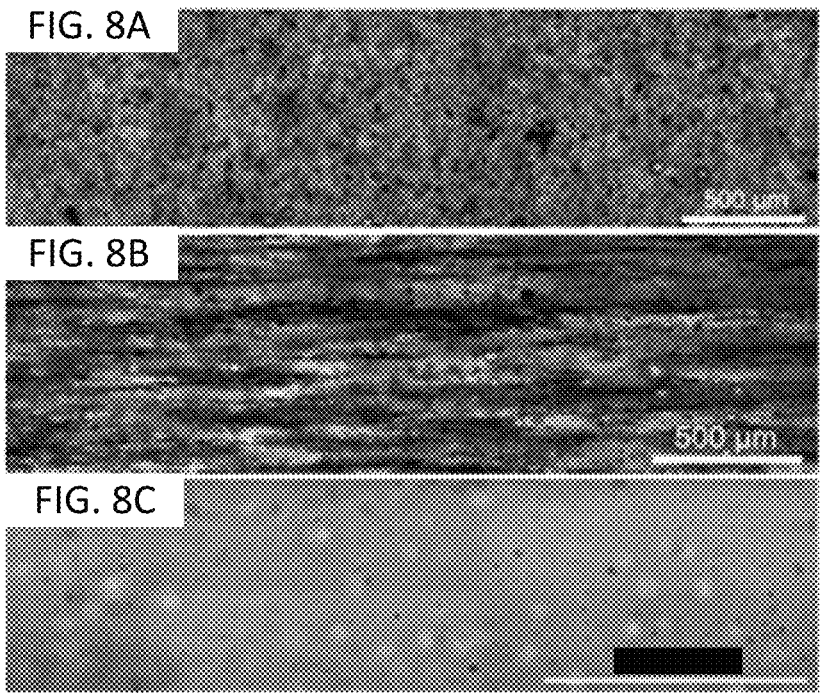
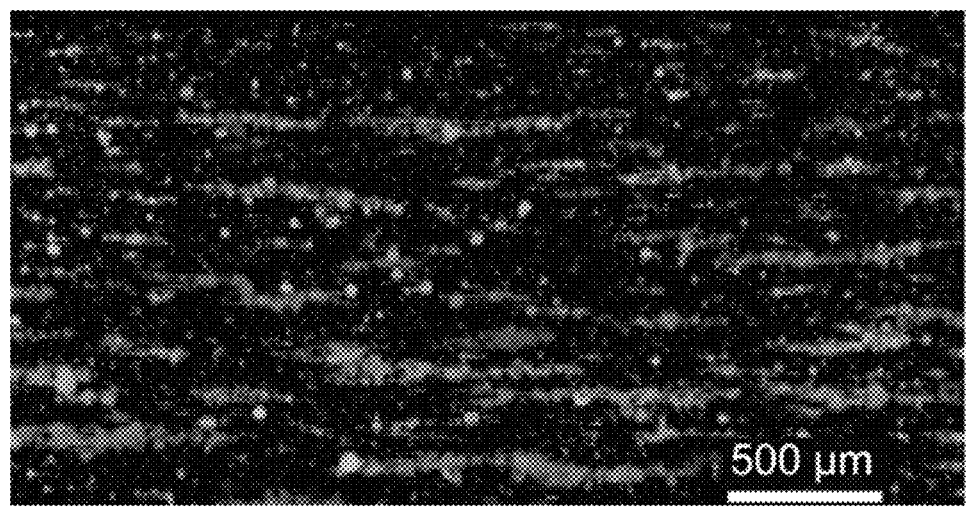
FIG. 9

MAGNETICALLY TEMPLATED TISSUE ENGINEERING SCAFFOLDS AND METHODS OF MAKING AND USING THE MAGNETICALLY TEMPLATED TISSUE ENGINEERING SCAFFOLDS

CROSS-REFERENCE TO RELATED APPLICATIONS

This application is a divisional of and claims priority to U.S. patent application Ser. No. 15/573,270, filed on Nov. 10, 2017 and titled "Magnetically Templated Tissue Engineering Scaffolds and Methods of Making and Using the Magnetically Templated Tissue Engineering Scaffolds", which was the 35 U.S.C. § 371 national stage application of PCT Application No. PCT/US2016/031794 having the same title, filed May 11, 2016, where the PCT claims priority to U.S. provisional application titled "Magnetically Templated Tissue Engineering Scaffolds and Methods of Making and Using the Magnetically Templated Tissue Engineering Scaffolds," having Ser. No. 62/160,202, filed on May 12, 2015, each of which are herein incorporated by reference in their entireties

STATEMENT REGARDING FEDERALLY SPONSORED RESEARCH OR DEVELOPMENT

This invention was made with government support under R21 NS093239 awarded by National Institutes of Health. The government has certain rights in this invention

BACKGROUND

Peripheral nerve injuries cause significant socioeconomic impact, resulting in over 8 million restricted activity days and over 5 million disability days per year. Over 200,000 peripheral nerve injury (PNI) repair procedures are performed each year in the US alone, with an estimated market for transected peripheral nerve injury repair of about $1.32-$1.93 billion in the US. Autograft remains the gold standard approach for repairing injuries with gaps greater than 2 cm, commonly from the patient's sural nerve. However, autografts result in significant morbidity and functional deficit at the donor site, their availability is limited, particularly for extensive lesions, and matching size of donor nerve to repaired nerve is often difficult. Furthermore, studies indicate motor function recovery occurs in only 40-50% of patients.

Alternative therapies involving processed nerve allografts obtained from decellularized cadaveric nerve tissue were developed. These studies were translated into the Avance® graft, which has achieved functional regeneration of nerve gaps up to 5 cm. Unfortunately, production of decellularized nerve allografts is limited by access to cadaveric tissue and is very costly because of the tedious and personnel-intensive procedure to clear the harvested nerve of undesired fat and connective tissue. In addition, as with any allograft, there is some remote chance of disease transmission. Other approaches, such as clinically available artificial nerve guides (e.g., Neuragen®) and other technologies under development have been unsuccessful in repairing transected PNI with gaps longer than 2 cm. Reported tissue engineering scaffolds for peripheral nerve injury repair that lack aligned channels have failed to meet the success of autografts for injuries greater than 20 mm.

SUMMARY

Briefly described, embodiments of the present disclosure provide a biocompatible tissue scaffold having aligned microchannels, methods of making magnetically templated tissue engineering scaffolds, and methods of repairing peripheral nerve damage.

An embodiment of the present disclosure provides a biocompatible tissue scaffold including a three-dimensional (3D) biocompatible scaffold material and a plurality of magnetically templated aligned microchannels having a diameter (e.g. about 1 µm to about 100 µm), wherein a portion of the microchannels or a network of interconnected microchannels, or both, extend the length of the scaffold.

Embodiments of methods for making a biocompatible, tissue scaffold having aligned microchannels include providing a biocompatible precursor material capable of polymerizing or crosslinking to form a gel or solid material upon activation; providing microparticles comprising one or more magnetic nanoparticles encapsulated in a dissolvable, biocompatible matrix material; combining the microparticles and the biocompatible liquid material in a mold; applying a magnetic field to the combined microparticles and biocompatible liquid such that the microparticles spatially align within the biocompatible material forming a plurality of columns of adjacent microparticles, where the columns are substantially directionally aligned with one another; activating the biocompatible precursor material to crosslink or polymerize such that the biocompatible material substantially solidifies, forming a three dimensional (3D) scaffold around the aligned microparticles; dissolving the matrix material of the microparticles to produce a plurality of aligned voids and microchannels within the scaffold; and allowing the dissolved matrix material and the released magnetic nanoparticles to diffuse out of the aligned voids and microchannels within the scaffold.

An embodiment of the present disclosure provides a biocompatible tissue scaffold having aligned microchannels formed by the methods of the present disclosure.

An embodiment of the present disclosure also provides methods of repairing peripheral nerve damage, which includes repairing a peripheral nerve gap with a biocompatible, magnetically templated tissue scaffold as described herein or a biocompatible tissue scaffold made by the method as described herein.

Other methods, compositions, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 2A-2C illustrate magnetic microparticles (FIG. 2A (optical) and FIG. 2B (SEM)) and formation of columnar structures of the microparticles in a scaffolding precursor material in a magnetic field (FIG. 2C, approximately 50 mT).

FIGS. 3A-3B illustrate use of a ring magnet to align microparticles in a scaffold precursor material (e.g., pre-hydrogel mixture) in a mold (FIG. 3A) and a formed hydrogel containing magnetic microparticles (sliced longitudinally) obtained from a the cylindrical mold in FIG. 3A after crosslinking.

FIGS. 6A-6C illustrate aligned commercial microparticles in water (FIG. 6A), GMHA pre-gel solution (FIG. 6B), and GMHA hydrogel (FIG. 6C).

FIGS. 7A-7C illustrate aligned alginate microparticles in water (FIG. 7a), GMHA pre-gel solution (FIG. 7B), and GMHA hydrogel (FIG. 7C).

FIGS. 8A-8C illustrate composite images of crosslinked GMHA hydrogels with unaligned microparticles (FIG. 8A), aligned microparticles (FIG. 8B), and aligned and degraded microparticles (FIG. 8C).

FIG. 9 Illustrates porous channels remaining after particle degradation.

DETAILED DESCRIPTION

Figure 1:
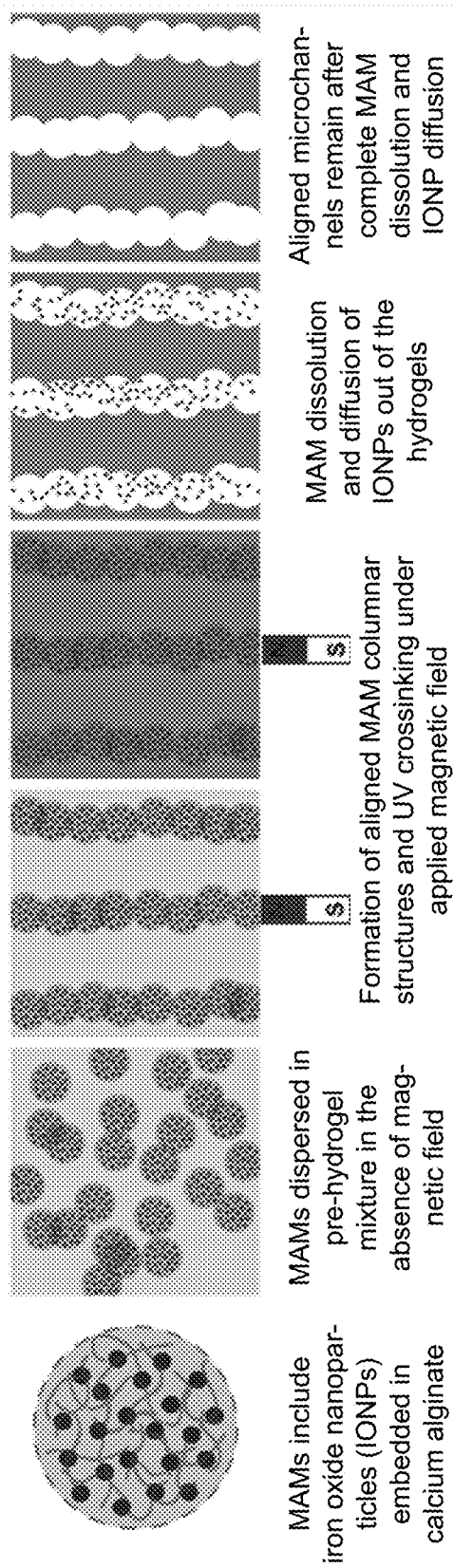
FIG. 1 is a schematic illustration of an embodiment of a method of the present disclosure for using magnetic microparticles for making microchannels in a scaffolding material to provide templated tissue scaffolds.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are incorporated by reference, as noted in the application, are incorporated by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of, chemistry, organic chemistry, organometallic chemistry, polymer chemistry, microbiology, tissue engineering, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

As used herein, the term "engineered" indicates that the engineered object is created and/or altered by man. An engineered object may include naturally derived substances, but the object itself is altered in some way by human intervention and design.

As used herein the term "channels" or "microchannels" refers to tubules or tube-like formations within a construct. The channels have a generally elongated and/or cylindrical shape, with a generally circular cross-section. The channels have an open (e.g., hollow or substantially hollow) interior (referred to herein as a "lumen") creating a via/conduit that forms a scaffold/template for the growth of cells/tissues and can also facilitate the movement of fluid, cells, and other materials within and/or through the construct. In embodiments, the microchannels can have a diameter in the micron range (e.g., 1-100 μm, including diameters from 5-20 μm, and diameters with an average of about 10 μm).

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

The term "biocompatible scaffold material" refers to any compound substance with sufficient structural stability to provide a substrate to support the growth of a living biological substance (e.g., living cells). In embodiments of the present disclosure the biocompatible scaffold material has a three-dimensional structure (rather than a planar, 2-dimensional structure) to support three-dimensional growth of living cells. In embodiments, the biocompatible scaffold material is made from a liquid/semi-liquid material that can be crosslinked and/or polymerized into a matrix that provides a more solid (e.g., solid, gel, semi-solid, etc.) scaffold.

The term "matrix material" refers to several different types of semi-solid to solid materials with a gel-like and/or solid consistency and a structure capable of supporting the growth of living biological substances (e.g., living cells). Both synthetic and naturally derived gel matrix materials exist and are in use by those of skill in the art. Gel matrix materials include hydrogels, such as biocompatible naturally derived or synthetic hydrogels, such as, but not limited to polymer-based hydrogels, PEG based hydrogels, alginate, cellulose, keratin, elastin, collagen, and the like. Gel matrix materials also include biocompatible polymer or copolymer based gel materials, such as polymer and copolymer based hydrogels. Gel matrix materials may also include a gelling agent or crosslinking agent (e.g., formaldehyde, glutaraldehyde, etc.) to increase the structural stability of the gel (e.g., to give it more "solid" characteristics).

As used herein, the term "solid" shall include "semi-solid" materials, and "liquid" shall include "semi-liquid" materials.

The term "polymer" includes any compound that is made up of two or more monomeric units covalently bonded to each other, where the monomeric units may be the same or different, such that the polymer may be a homopolymer or a heteropolymer. Representative polymers include polyamides, such as polypeptides, poly-N-substituted glycines (polypeptoids), polysaccharides, polyethylene glycol or polyethylene oxide, plastics (e.g., poly-L-lactic acid, poly-L-glutamic acid and co-polymers thereof), nucleic acids and the like, where the polymers may be naturally occurring, non-naturally occurring, or synthetic. The term "bio-polymer" refers to a polymer made of biologically-derived and/or biologically compatible compounds The term "attached" or the phrases "interacts with" and "associated with" refers to a stable physical, biological, biochemical, and/or chemical association. In general, association can be chemical bonding (e.g., covalently or ionically), a biological interaction, a biochemical interaction, and in some instances a physical interaction. The association can be a covalent bond, a non-covalent bond, an ionic bond, a metal ion chelation interaction, as well as moieties being linked through interactions such as, but not limited to, hydrophobic interactions, hydrophilic interactions such as hydrogel bonding, charge-charge interactions, π-stacking interactions, combinations thereof, and like interactions.

Use of the phrase "biomolecule" is intended to encompass deoxyribonucleic acid (DNA), ribonucleic acid (RNA), nucleotides, oligonucleotides, nucleosides, proteins, peptides, polypeptides, selenoproteins, antibodies, protein complexes, peptide nucleic acids, combinations thereof, and the like. In particular, the biomolecule can include, but is not limited to, naturally occurring substances such as polypeptides, polynucleotides, lipids, fatty acids, glycoproteins, carbohydrates, fatty acids, fatty esters, macromolecular polypeptide complexes, vitamins, co-factors, whole cells, eukaryotic cells, prokaryotic cells, microorganisms, or combinations thereof.

The phrase "bioactive agent" includes a biomolecule or other biocompatible compound that has some activity, use, and/or effect in a biological system or in relation to another biomolecule.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

DISCUSSION

In accordance with the purpose(s) of the present disclosure, as embodied and broadly described herein, embodiments of the present disclosure relate to magnetically templated tissue scaffolds, methods of making the scaffolds, and various methods of employing the scaffolds for tissue growth and repair in vitro and in vivo, peripheral nerve repair, and many other uses.

Tissue engineering scaffolds with aligned pores and channels are of interest in a variety of biomedical applications, including nerve injury repair. As discussed above, due to limitations in existing technologies for repair of peripheral nerve injury (PNI), a need exists for a bioengineered peripheral nerve scaffold that includes the architecture or both chemical and architectural components of natural peripheral nerve tissue to facilitate repair of any size nerve gaps, including longer nerve gaps, without the disadvantages of autografts, allografts, and existing nerve guide conduits. It is believed that the success of decellularized nerve allografts in repairing 2-5 cm gaps stems, at least in part, from preservation of the native basal lamina extracellular matrix (ECM) microstructure of the nerve. Specifically, preservation of approximately 10 μm diameter basal lamina tubes helps direct axonal growth and guide nerve reconnection. However, the fact that decellularized nerve allografts fail in repairing PNI with 5-12 cm gaps, for which autografts are successful, indicates that control over topography alone faces limitations in repair of long PNI gaps. Processing conditions used to obtain decellularized nerve allografts remove all chemical and biological cues that may aid in directing axonal growth, and incorporating these chemical and biological cues a posteriori has been challenging, particularly for long grafts. This may be a contributor to failure of nerve allografts in repairing gaps between about 5-12 cm. Thus, a need exists for regeneration scaffolds with tubular microstructure that mimics that of natural nerve, including aligned, gap-spanning tubes with a diameter comparable to natural peripheral nerve (e.g., approximately 10 μm) embedded in a biocompatible matrix and obtained through methods that are compatible with incorporating chemical and biological cues.

Magnetic fields to control nano- and microtopography, or to direct assembly of cells or tissue engineering scaffolds can be used in various applications. Alignment of collagen and fibrin fibers through magnetic fields has been studied to direct cell growth, but suffers practical limitations for PNI repair because fiber alignment relaxes once the magnetic field is removed. Magnetic alignment of anisotropic dissolvable particles has been used to create bone cement scaffolds with anisotropic porosity, but the reported materials lack the gap-spanning aligned microchannels required for PNI repair applications. Magnetic hydrogels have been reported that respond to magnetic fields because of magnetic nanoparticles retained within the hydrogel, but lack the tubular features required for PNI repair. Magnetic fields have also been used to direct 2D patterning of dissolvable magnetic sugar particles, leaving behind a scaffold with patterned 2D porosity, but the pores are too large to effectively direct axon growth and do not form continuous tubular guidance conduits that span dimensions relevant for PNI repair. Magnetic fields have also been used to direct assembly of cells and hydrogels, but not with the topographic features, nor at the size scales needed for PNI repair. The present disclosure provides magnetic templating distinct from the other approaches in its use of magnetic microspheres that form aligned, gap-spanning columnar structures and that, once dissolved, leave behind a tubular microstructure with dimensions suited for effective PNI repair.

The present disclosure provides a new approach to provide templated tissue scaffolds with controllable diameter and length, with aligned pores and microchannels to provide appropriate structure for growth of tissue, such as nerve tissue suitable for peripheral nerve repair. Briefly described, in embodiments, a magnetic field is applied to a mold containing a crosslinkable and/or polymerizable biocompatible precursor material (e.g. a biocompatible, polymerizable polymer, a crosslinkable or photopolymerizable hydrogel of naturally derived biomaterial, etc.) mixed with a plurality of sacrificial magnetic microparticles (e.g., microparticles of a sacrificial/dissolvable matrix material with encapsulated/embedded magnetic nanoparticles). The magnetic field causes the microparticles to align and form a plurality of lines/columns of adjacent microparticles, where the columns are also substantially aligned with each other (e.g., substantially oriented in the same direction, substantially parallel, etc.). In embodiments, the magnetic field is applied such that the microparticles substantially align to form columns along the length (e.g., greater dimension) of the mold (e.g., longitudinal rather than crosswise alignment). After allowing the particles to align, while still applying the magnetic field or immediately after removal of the magnetic field, appropriate stimulus is applied to the crosslinkable/polymerizable biocompatible material to activate the crosslinking/polymerization of the material (e.g., application of UV light for photopolymerizable materials, addition of a chemical crosslinker, heat activation, etc.). In embodiments the crosslinking/polymerization is done while still applying the magnetic field to ensure the magnetic microparticles remain in columns within the biocompatible precursor material. In some embodiments, the crosslinking/polymerization is done immediately after removing the material from the magnetic field such that the material polymerizes/crosslinks before the microparticle columns/chains disassemble (e.g., when the precursor material is somewhat viscous such that the microparticles do not diffuse out of alignment immediately).

Upon crosslinking/polymerizing of the material, the biocompatible material substantially solidifies (gel, solid/semisolid) to form a three dimensional (3D) scaffold around the aligned microparticles. After formation of the scaffold, the matrix material of the microparticles is dissolved/sacrificed, and the dissolved material and the magnetic nanoparticles diffuse/leach out of the scaffold through the microchannels and pores left behind by the microparticles. In embodiments, additional biomolecules (e.g., cells, proteins, carbohydrates, nucleic acids, etc.) may be included in the biocompatible scaffold material and/or matrix material of the microparticles, and all of the polymerizing/crosslinking/dissolution steps are carried out in biocompatible conditions that are non-toxic/non-harmful to any such biomolecules (e.g., they do not interfere with the intended purpose/activity of the biomolecules).

One of the principal functions of a biological scaffold is to direct cell behavior such as migration, proliferation, differentiation, maintenance of phenotype, etc. by facilitating sensing and responding to the environment via cell-matrix and cell-cell communications. In embodiments, the present disclosure provides crosslinked or polymerized scaffolds of biocompatible and/or naturally derived biomaterials containing aligned tubular microstructure that mimics natural nerve tissue through magnetic templating as shown in the embodiment illustrated in FIG. 1. With magnetic templating, the length, diameter, connectivity, and areal density of microchannels remaining after dissolution of magnetic microparticles can be tuned through control of microparticle concentration, diameter, and magnetic nanoparticle content, and through magnetic field conditions. Furthermore, the appropriate magnetic fields can be generated to obtain scaffolds that are ~12 cm long while permitting crosslinking of the hydrogel. Finally, choosing microparticle materials with mild dissolution conditions that are biocompatible allows incorporation of chemical and biological cues into the scaffold before or after templating.

In embodiments of the present disclosure, the scaffold material can include a matrix of a synthetic or naturally derived resorbable or nonresorbable material, where the matrix is prepared by crosslinking or polymerization of a biocompatible precursor matrix-forming material. In embodiments, the scaffold material is both biocompatible and biodegradable. In embodiments, the precursor material is initially in a liquid or semi-liquid state before crosslinking/polymerization so that the precursor material has sufficient fluid properties to allow movement of the microparticles within the precursor material prior to crosslinking/polymerization. The crosslinking/polymerization is performed in the presence of a collection of dissolvable magnetic microparticles and under the application of a magnetic field, or immediately after, which causes the alignment of the magnetic particles in aligned structures. In embodiments, the dissolvable magnetic microparticles have sizes in the range of about 100 nm to 100 µm. For some applications the magnetic microparticles have sizes in a range of about 10 to 50 microns. In other embodiments, the particles have sizes in intermediate ranges within the 100 nm to 100 µm range, depending on the desired diameter of the microchannels formed once the aligned microparticles have dissolved and diffused away. After crosslinking or polymerization of the scaffold matrix material, the scaffold is treated in such a way to dissolve the magnetic particles, removing their constituents and leaving empty voids and channels in the scaffold. These voids and channels may then direct growth, including directional growth, of cells in the scaffold. The voids and channels may also be modified during or post-preparation with cell adhesion factors and other desirable biomolecules. In embodiments, the voids and channels are aligned along a direction of the scaffold over a length of about 20 mm or more.

The magnetically templated regeneration scaffolds of the present disclosure may replace clinical use of processed nerve allografts and nerve autografts for 2-12 cm PNI gaps. Regeneration scaffolds with tubular microstructure and that can span gaps up to 5 cm, could repair gaps without the need of chemical and biological cues and could potentially replace processed nerve allografts, which successfully repair gaps up to 5 cm without the need of chemical or biological cues. In embodiments, magnetically templated regeneration scaffolds of the present disclosure with aligned microchannels that span gaps up to 12 cm long and incorporate chemical and biological cues can direct axon growth past the apparent 5 cm limit of topography. Such regeneration scaffolds could potentially eliminate the need of nerve autografts. Furthermore, the magnetically templated scaffolds of the present disclosure have potential applications for tissue engineering in other diseases/conditions beyond PNI repair.

In embodiments of the magnetically templated scaffolds of the present disclosure, naturally derived biomaterials were selected as building blocks of the proposed scaffolds because of their biocompatibility and inherent role in wound healing. In addition, when using natural scaffolds (e.g., extracellular matrix (ECM)-based scaffolds), there is less concern with immunogenicity; the body will inherently remodel natural materials, unlike with many synthetic materials in which there could be issues associated with toxicity and/or adverse effects associated with either the material itself or its degradation products. These features grant naturally derived biomaterials with potential for near term clinical success. However, the magnetic templating methods of the present disclosure are also compatible with hydrogels and other scaffolding materials made of synthetic biomaterials.

In an embodiment the biocompatible material for forming the scaffold is selected from a biocompatible, crosslinkable hydrogel. In embodiments, the biocompatible precursor material is in a liquid or semi-liquid form prior to crosslinking/polymerization into a gel/solid/semi-solid matrix that forms the biocompatible scaffold. Examples of biocompatible materials that can be used to form the scaffold of the present disclosure include, but are not limited to, hyaluronic acid, collagen, polyethylene glycol, fibrin, and the like. In embodiments, the scaffold material is formed from a chemically crosslinked hyaluronic acid hydrogel. Hyaluronic acid has advantageous features, such as, but not limited to: it is biodegradable and biocompatible, it is FDA approved (e.g., for use in dermal fillers), it is a natural component of extracellular matrix, it allows for incorporation of other chemical/biological factors, and it forms an amorphous solid. In another embodiment the scaffold material consists of suitable crosslinked collagen, which also shares many of the same advantages. Other biocompatible hydrogels and other biocompatible material may be employed as the scaffolding material. Also, combinations of such materials can also be used. For instance, in embodiments, the scaffolding material may include both hyaluronic acid and collagen and/or other matrix-forming materials.

In embodiments, the biocompatible material for forming the scaffold is initially in a liquid (including liquid and semi-liquid states) state but is capable of being crosslinked or polymerized to form a matrix material that is a gel, solid/semi-solid material upon activation (e.g., chemically or physically, such as, but not limited to application of UV light, application of heat, addition of a chemical crosslinker or activator, etc.). Once crosslinked/polymerized, the biocompatible material forms a matrix that provides a three-dimensional (3D) scaffold. In the embodiments of the present disclosure, this scaffold is formed around the microparticles, which are present in the biocompatible material prior to activation of the crosslinking/polymerization, such that the location of the microparticles leaves a void in the scaffold upon removal of the microparticle. Since the microparticles can be aligned by application of a magnetic field and then dissolved after scaffold formation, the adjacent voids created by the aligned microparticles form tubules or microchannels in the scaffold. By application of the magnetic field, the directional alignment of the microparticles can be controlled, such that in embodiments, the microchannels are substantially aligned along the length of the scaffolding material. In embodiments, a portion of the microchannels extend the full length of the scaffolding material. In embodiments, a portion of the microchannels extending the length of the scaffolding have an opening at each end of the scaffolding. In embodiments, the scaffolding material is formed in a mold to provide shape and support to the biocompatible scaffolding precursor material prior to crosslinking/polymerizing. The mold can be later removed. In embodiments, the mold is a sacrificial material that is later removed using known techniques.

In an embodiment of the templated tissue scaffold of the present disclosure and methods of making the scaffold, the microparticles include magnetic nanoparticles encapsulated in a dissolvable matrix. In embodiments, the dissolvable magnetic microparticles have sizes in the range of 100 nm to 100 µm. In an embodiment, the magnetic nanoparticles include iron oxide nanoparticles. In an embodiment, the magnetic nanoparticles are also combined with a surfactant, charged species, or polymer that confers colloidal stability in aqueous media. In embodiments, the dissolvable matrix material is a polymer matrix material. In embodiments, the matrix material is a biocompatible material such as, but not limited to, calcium alginate, a polyethylene glycol based hydrogel that dissolves in response to a stimulus, and the like. For embodiments where the matrix material is calcium alginate, the dissolution step may be performed using a sodium citrate, EDTA, and/or alginate-lyase solution. In an embodiment, the magnetic microparticles include tetramethyl ammonium hydroxide stabilized iron oxide nanoparticles encapsulated in calcium alginate to form microparticles through an emulsion crosslinking technique under optimized conditions to yield particles with diameters in the range of about 1-20 µm. In some embodiments, the magnetic particles have a mean diameter of about 10 µm. In embodiments, after activation and formation of the scaffolding material and dissolution of the microparticles, the formed microchannels have a diameter of about 1 to about 20 µm. In embodiments, the microchannels have an average diameter of about 10 µm. In some embodiments microfluidic devices can be used to create the alginate microparticles, which allows for size control in the 1-400 µm range. For instance, in embodiments, the magnetic microparticles include tetramethyl ammonium hydroxide stabilized iron oxide nanoparticles encapsulated in calcium alginate to form microparticles through microfluidic droplet formation using a flow focusing device, or other such devices suitable for making microdroplets.

In embodiments of the templated scaffolds and methods of the present disclosure, the synthetic or naturally derived biocompatible material may be resorbable or nonresorbable. In embodiments, the biocompatible scaffolding material may be biodegradable such that the scaffolding material degrades in vivo or in vitro over time. In some embodiments, the biocompatible scaffolding may contain living cells or other biomolecules prior to crosslinking or polymerization in the presence of magnetically aligned nanoparticles. Such cells or biomolecules would then be left behind in the scaffold material once the magnetic microparticles are dissolved. Such embodiments can provide controlled release of active agents into the pores or microchannels left after dissolution and leaching of the magnetic particles, providing biological cues that direct cell growth into the scaffold and phenotype differentiation within the scaffold.

Similarly, in some embodiments, the magnetic microparticles may include cells or biomolecules (such as, but no limited to, growth factors, enzymes, and the like) co-encapsulated with magnetic nanoparticles in the dissolvable matrix material. Then, upon dissolution of the particle matrix, the cells or biomolecules are left behind in the resulting pores and channels of the scaffold. This may be useful for rapidly populating large scaffolds with cells. It may also be useful for directing invasion, growth, and differentiation of cells in the scaffolds. One example application includes populating channels with Schwann cells, which may direct axonal growth into the scaffold. In embodiments, autologous cells from the recipient can be cultured and encapsulated in the pre-crosslinked or pre-polymerized scaffolding material and/or in the microparticle matrix as a way to seed the scaffold and/or the microchannels with recipient's cells to stimulate growth. In some embodiments, the presence of cells in the magnetic microparticles and in the scaffold matrix is combined.

The present disclosure includes templated scaffolds prepared by the processes including the methods of the present disclosure described above. Such magnetically templated tissue scaffolds include a three-dimensional, biocompatible, and optionally biodegradable, scaffolding material (e.g., a biocompatible hydrogel, a biocompatible polymer, etc.) that is formed from a precursor material that is crosslinkable/polymerizable under biocompatible conditions. In embodiments, magnetically templated tissue scaffolds of the present disclosure also include a plurality of magnetically templated aligned microchannels where a portion of the microchannels (as a single microchannel or a group of interconnected microchannels) extend the length of the scaffold such that, in combination, the connected microchannels span the length of the scaffold. In embodiments, at least a portion of the microchannels (single or interconnected) extend the length of the scaffold with openings at each end of the scaffold. In embodiments, the microchannels are at least substantially aligned with each other and are substantially directionally aligned along the length of the tissue scaffold. In embodiments, the microchannels have a diameter of 1 to about 20 µm. In embodiments, the microchannels have an average diameter of about 10 µm. In embodiments, the scaffold also includes living cells and/or other biomolecules within the scaffolding material and/or within the interior space (e.g., lumen) of the microchannels. In embodiments, the scaffolds have a length of about 2-12 cm, although in some embodiments, the scaffolds can have a length greater than 12 cm or less than 2 cm. In embodiments, the scaffolds have a length of about 2-5 cm. In embodiments, they have a length of about 5-12 cm. In embodiments, a least a portion of the microchannels within the scaffold extend the length of the scaffold and thus have a length (may be length of interconnected microchannels) between about 2-12 cm. In embodiments, a single microchannel spans the length of the scaffold; in other embodiments, some microchannels join with other microchannels to jointly span the length of the scaffold.

Embodiments of the present disclosure also include methods of inducing cell growth in the biocompatible, magnetically templated scaffolds of the present disclosure in vivo or in vitro. Methods also include methods of repairing peripheral nerve damage by using the biocompatible tissue scaffolds of the present disclosure to repair nerve gaps of about 2-12 cm, such as in the embodiment described in Example 2, below. Smaller nerve gap repair is also possible with the scaffolds and methods of the present disclosure, such as gaps smaller than 2 cm, e.g., from about 2 mm to about 2 cm. Typically, for a gap less than 2 mm, it can be surgically repaired without the need for a scaffolding material or graft.

Additional details regarding the methods and compositions of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the present disclosure, in general, the examples describe some additional embodiments of the present disclosure. While embodiments of present disclosure are described in connection with the examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Magnetically Templated Hyaluronan Hydrogel Tissue Scaffolds

Tissue engineering scaffolds (scaffolds) with aligned pores and channels can be useful for a variety of biomedical applications, including nerve injury repair. This example describes an embodiment of engineering scaffolds with aligned pore and channel structures through magnetically guided assembly of dissolvable magnetic particles.

The present example describes making and testing of magnetically templated scaffolds using magnetic alginate microparticles (MAMs) including biocompatible iron oxide nanoparticles embedded in a crosslinked calcium alginate matrix. Iron oxide nanoparticles are one component in various FDA approved magnetic resonance imaging contrast agents, and are believed to be biocompatible and bioabsorbable. Furthermore, in magnetic templating, the majority, if not all, of the iron oxide nanoparticles are removed during the MAM dissolution step. Alginate was selected as the dissolvable matrix for the MAMs due, at least in part, to its biocompatibility, its use to encapsulate viable cells for culture, and because dissolution can be achieved under mild conditions that do not affect biomolecules or cell viability, such as described in the following references, which are hereby incorporated by reference herein (W. R. Gombotz and S. F. Wee, "Protein release from alginate matrices," Advanced Drug Delivery Reviews, vol. 64, pp. 194-205, 2012; H. H. Tønnesen and J. Karlsen, "Alginate in drug delivery systems," Drug development and industrial pharmacy, vol. 28, pp. 621-630, 2002; and C. Bucke, "Cell Immobilization in Calcium Alginate," Methods in enzymology, vol. 135, pp. 175-189, 1987). These qualities of alginate encapsulated microparticles are compatible with embodiments where cells or biomolecules are incorporated into the scaffold or microparticles to provide chemical and biological cues.

In the present example, hyaluronan hydrogels containing collagen as the base biomaterial were employed. Hyaluronan (HA) is a natural component of adult brain and spinal cord ECM, is biocompatible, non-immunogenic, and is easy to modify. Collagen, while less prevalent in the adult brain, has been successfully combined with HA to enhance cell adhesion properties in nerve tissue repair applications. Both HA and collagen biodegrade into harmless natural components. Due to these features HA/collagen hydrogels were selected as suitable material for the scaffolding matrix in the magnetically templated regeneration scaffolds.

To illustrate feasibility, MAMs were obtained by water-in-oil emulsion crosslinking of sodium alginate and iron oxide nanoparticle mixtures using calcium chloride. The iron oxide nanoparticles were synthesized and peptized according to procedures described in Mérida, A. Chiu, A. Bohórquez, L. Maldonado, M.-E. Pérez, L. Pericchi, M. Torres-Lugo, C. Rinaldi, "Optimization of synthesis and peptization steps to obtain iron oxide nanoparticles with high specific absorption rates." *Journal of Magnetism and Magnetic Materials*, 394:361-371, 2015, which is hereby incorporated by reference herein. Briefly, aqueous solutions of iron (II) and iron (III) salts are prepared in degassed deionized water (total metal concentration of 0.3 M, with 2:1 $Fe^{3+}$:$Fe^{2+}$ molar ratio). These solutions are then heated and $NH_4OH$ added, followed by one-hour reaction at elevated temperature (85° C.). The pH was kept between 8.0 and 9 using $NH_4OH$. The resultant nanoparticle solution was cooled to room temperature, centrifuged, and magnetically decanted. Peptization with tetramethylammonium hydroxide (TMAOH) was achieved using a IO/TMAOH volume ratio of 2 by dispersing the iron oxide nanoparticles in the peptizing agent followed by application of ultrasound (XL2020, Misonix Inc.). The resulting nanoparticles were centrifuged and magnetically decanted, dried overnight, and then suspended in water to yield aqueous nanoparticle solutions, which were used as stock solutions for further use.

For emulsion MAM production, an aqueous phase of 20 mg/mL sodium alginate and 10-200 mg/mL Iron Oxide Peptized Nanoparticles in $H_2O$ was added dropwise to the continuous phase of mineral oil with 5% Span 80 surfactant while shearing on a homogenizer for ~10 minutes at 4000 RPM. 10% CaCl solution was then added at a rate of 3 mL/min to crosslink the alginate, and homogenization was continued for 3 minutes for complete mixing and alginate gelation. After homogenization, the solution was added to 100% EtOH, and the particles were separated from the continuous phase using either centrifugation or magnetic separation. Using either method, the supernatant was discarded after separation, and the particles were resuspended in 100% EtOH for at least 4 washes. After particle purification, the particles were resuspended in DI $H_2O$ and aliquoted into pre-weighted tubes for lyophilization to determine the dried weight of particles. Particles were stored in a desiccator at −20° C. and resuspended in water at known concentrations prior to use. Optical microscopy and scanning electron microscopy indicate these MAMs were irregular in shape and polydisperse in size, with diameters of up to 5 μm (FIGS. 2A and 2B).

MAMs are easily dispersed in HA/collagen pre-hydrogel mixtures and readily align into long columnar structures upon application of a magnetic field (FIG. 2C). The length of these columnar structures appears to be determined by the size of the magnet used and the concentration of the particles in the pre-hydrogel mixture, and alignment for hydrogels >2 cm long was achieved using a cylinder magnet (FIGS. 3A &3B). The cylindrical magnet used in the present example was a RX08X0 magnet from K&J Magnetics. Using GMHA hydrogels, the maximum particle concentration that can be added appears governed by the ability of UV light to penetrate the hydrogel for GMHA crosslinking. Hydrogel gelation has been shown to occur up to MAM concentrations of 10-20 mg/mL, dependent on MAM synthesis conditions, magnetic nanoparticle concentration, average MAM diameter, and overall purity.

Figures 4A, 4B, 4C:
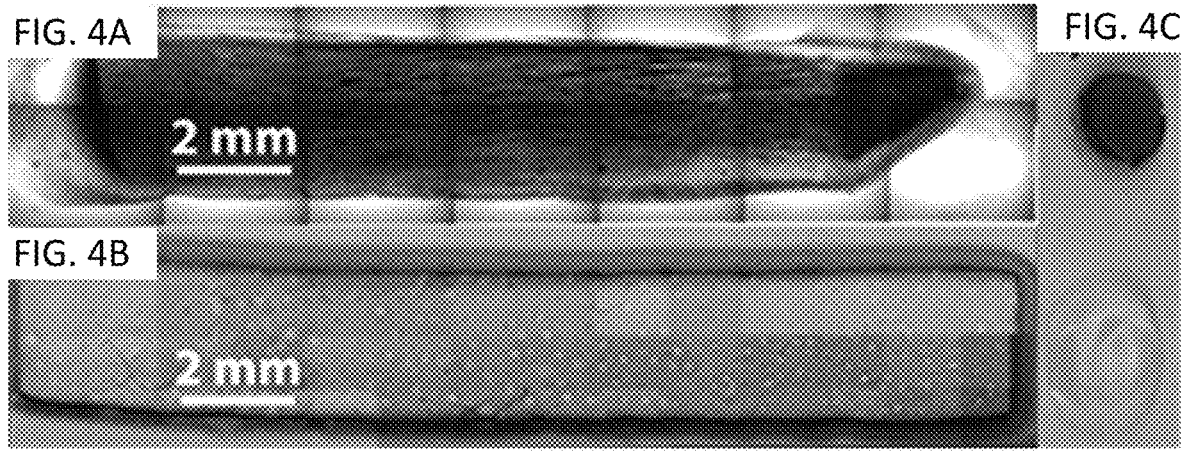
FIGS. 4A-4B illustrate a crosslinked hydrogel of approximately 10 mm in length, showing a columnar magnetic microparticle structure before dissolution of the particles (FIG. 4A) and the microchannels remaining after dissolution of the microparticles in EDTA (FIG. 4B).
FIG. 4C illustrates cross sections of similar hydrogels corresponding to FIGS. 4A and 4B before (above) and after (below) dissolution.

Columnar structures were preserved under the magnetic field during crosslinking of the HA/collagen hydrogel using UV (FIG. 4A), and the MAMs readily dissolve using the $Ca^{2+}$ chelating agents (FIG. 4B).

Figure 5:
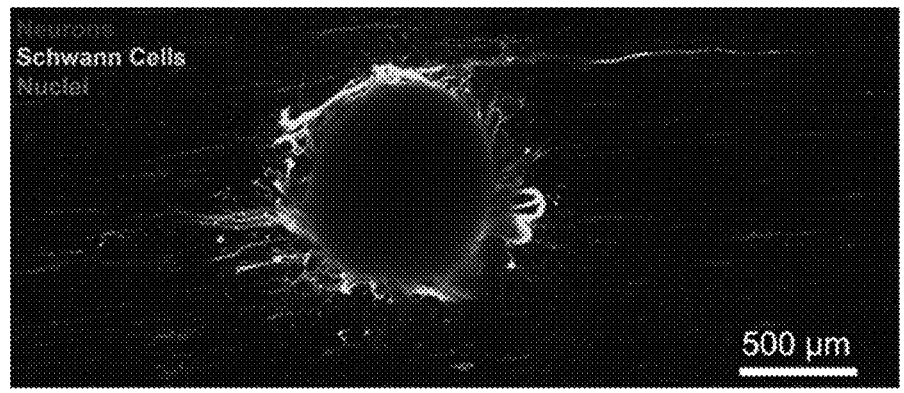
FIG. 5 illustrates neurite ingrowth of GFP+P1 rat dorsal root ganglia (DRG) on templated HA+collagen I hydrogel, demonstrating the ability to create templated tissue scaffolds to support cell attachment and growth.

In this study, EDTA was used to dissolve the MAMs. While EDTA is compatible with the presence of some biomolecules, it may be replaced with other dissolution compounds in embodiments that incorporate cells into the hydrogels. For example, MAMs can also be dissolved using sodium citrate, which is commonly used to dissolve alginate beads used to encapsulate cells in 3D cell culture. Alginate-lyase can be used to enzymatically degrade the alginate into smaller MW fragments for more rapid diffusion through the hydrogel matrix. Finally, preliminary studies of in vitro ingrowth of rat dissociated dorsal root ganglia (DRG) into HA/collagen hydrogels with templated channels indicates this base biomaterial is suitable for scaffolds to direct axon growth (FIG. 5).

Additional methods and templated tissue scaffolds were also demonstrated. A comparison of the results utilizing commercial microparticles and the alginate microparticles described above is shown in FIGS. 6A-6C and FIGS. 7A-7C. Aligned commercial microparticles (Bangs Laboratories Inc., PMC3N, ProMag™ 3 μm diameter polymer-based magnetite spheres) are shown in water (FIG. 6A), GMHA pre-gel solution (FIG. 6B), and GMHA hydrogel (FIG. 6C). Aligned alginate microparticles made as described above are shown in water (FIG. 7A), GMHA pre-gel solution (FIG. 7B), and GMHA hydrogel (FIG. 7C). FIGS. 8A-8C illustrate composite images of crosslinked GMHA hydrogels made as described above with unaligned alginate microparticles (FIG. 8A), aligned alginate microparticles (FIG. 8B), and aligned and degraded alginate microparticles (FIG. 8C). Finally, FIG. 9 Illustrates porous channels remaining after particle degradation. The channels were imaged under confocal microscopy after backfilling with Dextran-FITC.

REFERENCES FOR EXAMPLE 1

[1] J. S. Belkas, M. S. Shoichet, and R. Midha, "Axonal guidance channels in peripheral nerve regeneration," *Operative Techniques in Orthopaedics*, vol. 14, pp. 190-198, July 2004.
[2] S. Ichihara, Y. Inada, and T. Nakamura, "Artificial nerve tubes and their application for repair of peripheral nerve injury: an update of current concepts," Injury, vol. 39, pp. 29-39, October 2008.
[3] K. Brattain, "Analysis of the Peripheral Nerve Injury Market in the United States," Magellan Medical Technology Consultants, Inc., Minneapolis, MN, 2013.
[4] S. K. Lee and S. W. Wolfe, "Peripheral nerve injury and repair," *J Am Acad Orthop Surg*, vol. 8, pp. 243-52, July-August 2000.
[5] T. W. Hudson, S. Y. Liu, and C. E. Schmidt, "Engineering an improved acellular nerve graft via optimized chemical processing," *Tissue engineering*, vol. 10, pp. 1346-1358, 2004.
[6] T. W. Hudson, S. Zawko, C. Deister, S. Lundy, C. Y. Hu, K. Lee, and C. E. Schmidt, "Optimized acellular nerve graft is immunologically tolerated and supports regeneration," *Tissue engineering*, vol. 10, pp. 1641-1651, 2004.
[7] D. N. Brooks, R. V. Weber, J. D. Chao, B. D. Rinker, J. Zoldos, M. R. Robichaux, S. B. Ruggeri, K. A. Anderson, E. E. Bonatz, S. M. Wisotsky, M. S. Cho, C. Wilson, E. O. Cooper, J. V. Ingari, B. Safa, B. M. Parrett, and G. M. Buncke, "Processed nerve allografts for peripheral nerve reconstruction: a multicenter study of utilization and outcomes in sensory, mixed, and motor nerve reconstructions," *Microsurgery*, vol. 32, pp. 1-14, January 2012.
[8] E. C. Spivey, Z. Z. Khaing, J. B. Shear, and C. E. Schmidt, "The fundamental role of subcellular topography in peripheral nerve repair therapies," *Biomaterials*, vol. 33, pp. 4264-4276, Jul. 1 2012.
[9] S. Kehoe, X. F. Zhang, and D. Boyd, "FDA approved guidance conduits and wraps for peripheral nerve injury: A review of materials and efficacy," *Injury*, vol. 43, pp. 553-572, Jun. 1 2012.
[10] D. Hoffman-Kim, J. A. Mitchel, and R. V. Bellamkonda, "Topography, Cell Response, and Nerve Regeneration," *Annual Review of Biomedical Engineering*, vol. 12, pp. 203-231, July 2010.
[11] V. Mukhatyar, L. Karumbaiah, J. Yeh, and R. Bellamkonda, "Tissue Engineering Strategies Designed to Realize the Endogenous Regenerative Potential of Peripheral Nerves," *Advanced Materials*, pp. NA-NA, Nov. 10 2009.
[12] T. Hadlock, C. Sundback, D. Hunter, M. Cheney, and J. P. Vacanti, "A polymer foam conduit seeded with Schwann cells promotes guided peripheral nerve regeneration," *Tissue Eng*, vol. 6, pp. 119-27, April 2000.
[13] S. Stokols and M. H. Tuszynski, "Freeze-dried agarose scaffolds with uniaxial channels stimulate and guide linear axonal growth following spinal cord injury," *Biomaterials*, vol. 27, pp. 443-451, February 2006.
[14] J. B. Scott, M. Afshari, R. Kotek, and J. M. Saul, "The promotion of axon extension in vitro using polymer-templated fibrin scaffolds," *Biomaterials*, vol. 32, pp. 4830-4839, Jul. 1 2011.
[15] K. T. Morin and R. T. Tranquillo, "Guided sprouting from endothelial spheroids in fibrin gels aligned by magnetic fields and cell-induced gel compaction," *Biomaterials*, vol. 32, pp. 6111-6118, Sep. 1 2011.
[16] N. Dubey, P. C. Letourneau, and R. T. Tranquillo, "Guided neurite elongation and Schwann cell invasion into magnetically aligned collagen in simulated peripheral nerve regeneration," *Experimental neurology*, vol. 158, pp. 338-350, 1999.
[17] D. Ceballos, X. Navarro, N. Dubey, G. Wendelschafer-Crabb, W. R. Kennedy, and R. T. Tranquillo, "Magnetically aligned collagen gel filling a collagen nerve guide improves peripheral nerve regeneration," *Experimental neurology*, vol. 158, pp. 290-300, 1999.
[18] R. T. Tranquillo, T. S. Girton, B. A. Bromberek, T. G. Triebes, and D. L. Mooradian, "Magnetically orientated tissue-equivalent tubes: application to a circumferentially orientated media-equivalent," *Biomaterials*, vol. 17, pp. 349-357, 1996.
[19] M. R. Sommer, R. M. Erb, and A. R. Studart, "Injectable Materials with Magnetically Controlled Anisotropic

[20] Y. Li, G. Huang, X. Zhang, B. Li, Y. Chen, T. Lu, T. J. Lu, and F. Xu, "Magnetic Hydrogels and Their Potential Biomedical Applications," *Advanced Functional Materials*, vol. 23, pp. 660-672, Sep. 27 2012.

[21] C. Hu, C. Tercero, S. Ikeda, M. Nakajima, H. Tajima, Y. Shen, T. Fukuda, and F. Arai, "Biodegradable porous sheet-like scaffolds for soft-tissue engineering using a combined particulate leaching of salt particles and magnetic sugar particles," *JBIOSC*, vol. 116, pp. 126-131, Jul. 1 2013.

[22] C. Hu, T. Uchida, C. Tercero, S. Ikeda, K. Ooe, T. Fukuda, F. Arai, M. Negoro, and G. Kwon, "Development of biodegradable scaffolds based on magnetically guided assembly of magnetic sugar particles," *Journal of Biotechnology*, vol. 159, pp. 90-98, Jun. 31 2012.

[23] B. R. Whatley, X. Li, N. Zhang, and X. Wen, "Magnetic-directed patterning of cell spheroids," *Journal of Biomedical Materials Research Part A*, vol. 102, pp. 1537-1547, Jul. 2 2013.

[24] S. Tasoglu, D. Kavaz, U. A. Gurkan, S. Guven, P. Chen, R. Zheng, and U. Demirci, "Paramagnetic Levitational Assembly of Hydrogels," *Advanced Materials*, vol. 25, pp. 1137-1143, Dec. 10 2012.

[25] L. H. Reddy, J. L. Arias, J. Nicolas, and P. Couvreur, "Magnetic Nanoparticles: Design and Characterization, Toxicity and Biocompatibility, Pharmaceutical and Biomedical Applications," *Chemical Reviews*, vol. 112, pp. 5818-5878, Nov. 14 2012.

[26] N. Lewinski, V. Colvin, and R. Drezek, "Cytotoxicity of Nanoparticles," *Small*, vol. 4, pp. 26-49, Feb. 18 2008.

[27] W. R. Gombotz and S. F. Wee, "Protein release from alginate matrices," *Advanced Drug Delivery Reviews*, vol. 64, pp. 194-205, 2012.

[28] H. H. Tønnesen and J. Karlsen, "Alginate in drug delivery systems," *Drug development and industrial pharmacy*, vol. 28, pp. 621-630, 2002.

[29] C. Bucke, "Cell Immobilization in Calcium Alginate," *Methods in enzymology*, vol. 135, pp. 175-189, 1987.

[30] Z. Z. Khaing and C. E. Schmidt, "Advances in natural biomaterials for nerve tissue repair," *Neuroscience Letters*, vol. 519, pp. 103-114, Jul. 25 2012.

[31] S. K. Seidlits, Z. Z. Khaing, R. R. Petersen, J. D. Nickels, J. E. Vanscoy, J. B. Shear, and C. E. Schmidt, "The effects of hyaluronic acid hydrogels with tunable mechanical properties on neural progenitor cell differentiation," *Biomaterials*, vol. 31, pp. 3930-3940, Jun. 1 2010.

[32] A. P. Herrera, C. Barrera, and C. Rinaldi, "Synthesis and functionalization of magnetite nanoparticles with aminopropylsilane and carboxymethyldextran," *Journal of Materials Chemistry*, vol. 18, p. 3650, 2008.

[33] V. L. Calero-DdelC, A. M. Gonzalez, and C. Rinaldi, "A Statistical Analysis to Control the Growth of Cobalt Ferrite Nanoparticles Synthesized by the Thermodecomposition Method," *Journal of Manufacturing Science and Engineering*, vol. 132, p. 030914, 2010.

[34] C. E. Schmidt and J. B. Leach, "Neural tissue engineering: strategies for repair and regeneration," *Annu Rev Biomed Eng*, vol. 5, pp. 293-347, 2003.

[35] S. Suri and C. E. Schmidt, "Photopatterned collagen-hyaluronic acid interpenetrating polymer network hydrogels," *Acta Biomater*, vol. 5, pp. 2385-97, September 2009.

[36] P. Danhier, G. De Preter, S. Boutry, I. Mahieu, P. Leveque, J. Magat, V. Haufroid, P. Sonveaux, C. Bouzin, O. Feron, R. N. Muller, B. F. Jordan, and B. Gallez, "Electron paramagnetic resonance as a sensitive tool to assess the iron oxide content in cells for MRI cell labeling studies," *Contrast media & molecular imaging*, vol. 7, pp. 302-307, May 26 2012.

[37] V. Ayala, A. P. Herrera, M. Latorre-Esteves, M. Torres-Lugo, and C. Rinaldi, "Effect of surface charge on the colloidal stability and in vitro uptake of carboxymethyl dextran-coated iron oxide nanoparticles," *Journal of Nanoparticle Research*, vol. 15, p. 1874, Jul. 30 2013.

[38] S. K. Seidlits, C. E. Schmidt, and J. B. Shear, "High-Resolution Patterning of Hydrogels in Three Dimensions using Direct-Write Photofabrication for Cell Guidance," *Advanced Functional Materials, vol.* 19, pp. 3543-3551, Nov. 23 2009.

[39] P. Dinh, A. Hazel, W. Palispis, S. Suryadevara, and R. Gupta, "Functional assessment after sciatic nerve injury in a rat model," *Microsurgery*, vol. 29, pp. 644-9, 2009.

Example 2

Three-Dimensionally Templated Hydrogels for Rat Sciatic Nerve Injury Repair

The present example describes an embodiment of a method for templating natural hydrogels with a linearly-oriented, three-dimensional porous architecture, which mimics the architecture of native peripheral nerve.

The present example describes making a bioengineered peripheral nerve repair scaffold including both chemical and architectural components of the natural peripheral nerve for repair of long nerve gaps. Hydrogel nerve repair scaffolds were developed using natural extracellular matrix components, with three-dimensional porous architecture similar to native nerve via templating with linearly-aligned, degradable magnetic microparticles.

In the present example, glycidyl methacrylated hyaluronic acid hydrogels were synthesized with 1.5 mg/mL Collagen I incorporated to allow for cell adhesion (GMHA-Col hydrogels). GMHA was dissolved at 2× the desired final concentration in 1% Irgacure 2959 (I2959, photocrosslinking initiator) and water overnight under agitation. Collagen I solution and MAMs were added, and sufficient H2O was added to bring the solution to the final dilution volume. Ultimately, the pre-gel solution contained 20 mg/mL GMHA, 0.3% I2959, 1.5 mg/mL Collagen 1, and 6 mg/mL MAMs. The pre-gel solution was mixed on an asymmetrical mixer (FlackTek) for uniform mixture all components and dispersion of MAMs.

Magnetic alginate microparticles (MAMs) were prepared via emulsification, using alginic acid and magnetite nanoparticles as described in Example 1, above.

The MAMs were added to the GMHA-Col hydrogel solution prior to gelation. The solution was injected into a silicone mold placed between 2 glass slides, and the mold was placed within a cylindrical magnet (as described in Example 1 above) for 20 minutes for particle alignment. After alignment, the molds were removed from the magnet and immediately placed under UV light for 10 minutes to crosslink the GMHA, followed by 40 minutes of incubation at 37° C. to induce collagen fibrillogenesis. Magnetic alginate microparticles were dissolved using alternating washes in 0.1M EDTA and 2 unit/mL alginate lyase for 12 days at 37° C. (three cycles of 1 day alginate lyase, 3 days EDTA). In other experiments, EDTA washes were shortened to 2 days each (total 9 days), which successfully dissolved the particles (data not shown). Finally, the hydrogels were equilibrated in DMEM base culture media for 1 week to remove residual EDTA and alginate-lyase.

Resulting templated hydrogels were wrapped with decellularized, small-intestinal submucosa (SIS) to create hydrogel implants capable of being sutured. In vivo sciatic nerve implants were conducted in Lewis rats using 3 experimental groups: isograft fresh-nerve repair, templated GMHA-Col hydrogels made as described above, and non-templated GMHA-Col hydrogels with identical hydrogel composition to the templated group except without the addition/dissolution of magnetic alginate microparticles. For each group, 8 mm of sciatic nerve was removed to create a 10 mm nerve gap with tension-free repair after implantation of the experimental device. Implants were harvested at 2 and 4-week endpoints (n=3 per group at each endpoint), for sectioning and immunohistochemical analysis.

Figure 10A:
FIGS. 10A-10B illustrate templated (FIG. 10A) and non-templated (FIG. 10B) hydrogels after 2 weeks of implantation in a rat sciatic nerve defect.
Figure 10B:
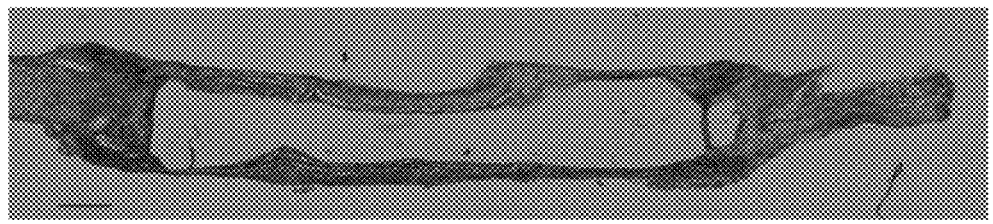

The present example demonstrates successful templating of GMHA-Col hydrogels using aligned magnetic particles. Particle alignment of densely-packed particle chains with millimeter-scale alignment length and tunable diameters of 10-100 μm was achieved. The particles were successfully degraded from crosslinked hydrogels, leaving behind porous channels. All rats survived implantation surgeries and recovered successfully through to the designated endpoints. Preliminary analysis of longitudinal sections clearly demonstrates greater cellular infiltration and hydrogel remodeling in templated GMHA-Col hydrogels vs. non-templated controls after 2 weeks of implantation (FIGS. 10A and 10B). Furthermore, templated hydrogel implants appear to be significantly degraded at 2 weeks, as compared to non-templated hydrogels that are primarily intact. This earlier degradation is desirable since with the formation of a fibrin cable is not necessary with the templated hydrogel implants of the present disclosure, which allows more rapid remodeling of nerve fibers.

The invention claimed is:

1. A biocompatible tissue scaffold for use in peripheral nerve repair comprising:
    (i) a three-dimensional (3D) biocompatible hydrogel scaffold, wherein the biocompatible hydrogel scaffold comprises a hyaluronic acid hydrogel; and
    (ii) a plurality of aligned voids and aligned microchannels, the voids and microchannels having a mean diameter of about 10 μm and being substantially directionally aligned along the length of the biocompatible scaffold,
    wherein the aligned voids and microchannels form networks of interconnected microchannels wherein at least a portion of the interconnected microchannels extend the length of the biocompatible tissue scaffold.

2. The biocompatible tissue scaffold of claim 1, wherein the aligned voids and microchannels are magnetically templated.

3. The biocompatible tissue scaffold of claim 1, wherein the biocompatible hydrogel scaffold material is biodegradable.

4. The biocompatible tissue scaffold of claim 1, wherein the hyaluronic acid hydrogel further comprises collagen.

5. The biocompatible tissue scaffold of claim 1, wherein the scaffold is about 2 to 12 cm in length.

6. The biocompatible tissue scaffold of claim 5, wherein at least a portion of the aligned voids and microchannels are about 2 to 12 cm in length.

7. The biocompatible tissue scaffold of claim 1, wherein at least a portion of the aligned voids and microchannels are about 2 to 12 cm in length.

8. The biocompatible tissue scaffold of claim 1, further comprising cells, biomolecules, or both, wherein the cells, biomolecules, or both are located in the aligned voids and microchannels, in the biocompatible hydrogel scaffold material, or in both.

9. A method of repairing peripheral nerve damage, comprising repairing a peripheral nerve gap with the biocompatible tissue scaffold of claim 1.

10. The method of claim 9, wherein the nerve gap is about 2-12 cm in length.

11. The method of claim 9, wherein the biocompatible tissue scaffold includes cells, biomolecules, or both and wherein the cells, biomolecules, or both are located in the aligned voids and microchannels, in the biocompatible scaffold material, or in both.

* * * * *